US011815434B2

(12) United States Patent
Pitzalis

(10) Patent No.: US 11,815,434 B2
(45) Date of Patent: Nov. 14, 2023

(54) METHOD FOR TREATING RHEUMATOID ARTHRITIS

(71) Applicant: Queen Mary University of London, London (GB)

(72) Inventor: Costantino Pitzalis, London (GB)

(73) Assignee: Queen Mary University of London

( * ) Notice: Subject to any disclaimer, the term of this patent is extended or adjusted under 35 U.S.C. 154(b) by 956 days.

(21) Appl. No.: 16/572,432

(22) Filed: Sep. 16, 2019

(65) Prior Publication Data

US 2020/0081006 A1    Mar. 12, 2020

Related U.S. Application Data

(62) Division of application No. 15/326,620, filed as application No. PCT/GB2015/052088 on Jul. 17, 2015, now Pat. No. 10,416,159.

(30) Foreign Application Priority Data

Jul. 17, 2014   (GB) .................................. 1412736

(51) Int. Cl.
| | | |
|---|---|---|
| *A61P 37/06* | (2006.01) | |
| *G01N 33/569* | (2006.01) | |
| *G01N 33/50* | (2006.01) | |
| *G01N 33/68* | (2006.01) | |
| *C07K 16/28* | (2006.01) | |
| *G01N 33/564* | (2006.01) | |

(52) U.S. Cl.
CPC ... *G01N 33/56972* (2013.01); *C07K 16/2866* (2013.01); *G01N 33/5052* (2013.01); *G01N 33/5082* (2013.01); *G01N 33/5094* (2013.01); *G01N 33/564* (2013.01); *G01N 33/6893* (2013.01); *C07K 2317/24* (2013.01); *C07K 2317/76* (2013.01); *G01N 2333/5412* (2013.01); *G01N 2333/70596* (2013.01); *G01N 2800/102* (2013.01); *G01N 2800/52* (2013.01)

(58) Field of Classification Search
None
See application file for complete search history.

(56) References Cited

FOREIGN PATENT DOCUMENTS

WO   WO 2012118750 A2   9/2012

OTHER PUBLICATIONS

Al-Shakarchi et al., Current perspectives on tocilizumab for the treatment of rheumatoid arthritis: a review, Patient Preference and Adherence 7:653-666, 2013.
Boumans et al., Response to Rituximab in Patients with Rheumatoid Arthritis in Different Compartments of the Immune System, Arthritis & Rheumatism 63:3187-3194, 2011.
Canete et al., Clinical significance of synovial lymphoid neogenesis and its reversal after anti-tumour necrosis factor alpha therapy . . . , Ann. Rheum. Dis. 68:751-756, 2009.
Dass et al., Highly Sensitive B Cell Analysis Predicts Response to Rituximab Therapy in Rheumatoid Arthritis, Arthritis & Rheumatism 58:2993-2999, 2008.
Gutierrez-Roelens et al., Rituximab Treatment Induces the Expression of Genes Involved in Healing Processes . . . , Arthritis & Rheumatism 63:1246-1254, 2011.
Humby et al., Ectopic Lymphoid Structures Support Ongoing Production of Class-Switched Autoantibodies in Rheumatoid Synovium, PLoS Med 6e1:0059-0075, 2009.
Kavanaugh et al., Assessment of rituximab's immunomodulatory synovial effects (ARISE trial). 1: clinical and synovial biomarkers results, Ann. Rheum. Dis. 67:402-408, 2008.
Kiesier et al., Disease Amelioration with Tocilizumab in a Treatment-Resistant Patient with Neuromyelitis Optica . . . , JAMA Neurol. 70:390-393, 2013.
Klaasen et al., The value of rheumatoid factor and anti-citrullinated protein antibodies as preditors of response to infliximab . . . , Rheumatol. 50:1487-1493, 2011.
Lal et al., Inflammation and Autoantibody Markers Identify Rheumatoid Arthritis Patients with Enhanced Clinical Benefit . . . , Arthritis & Rheumatism 63:3681-3691, 2011.
Mahto et al., Synovial B-Cells Predict Response/Resistance to Rituximab Therapy in Rheumatoid Arthritis . . . , Rheumatol. 53 Suppl. 1:i98, Abstract 107, 2014.
Mahto et al., Baseline synovial B-Cell status predicts response to rituximab therapy in RA, Ann. Rheum. Dis. J, 73 Suppl. 2, Abstract OP0032, 2014.
Manzo et al., Secondary and extopic lympoid tissue responses in rheumatoid arthritis: from inflammation to autoimmunity . . . , Immunolog. Rev. 233:267-285, 2010.
Manzo et al., Systematic microanatomical analysis of CXCL13 and CCL21 in situ production and progressive lympoid organization . . . , Eur. J. Immunol. 35:1347-1359, 2005.
Morel et al., Prospective Follow-up of Tocilizumab Treatment in 764 Patients with Refractory Rheumatoid Arthritis . . . , Arthritis & Rheumatism 64 Suppl. 5:S152, 2012.
Owczarczyk et al., A Plasmablast Biomarker for Nonresponse to Antibody Therapy to CD20 in Rheumatoid Arthritis, Sci. Transl. Med. 3:101ra92, 2011.
Patent Cooperation Treaty, International Search Report for Appln. No. PCT/GB2015/052088 (dated Jan. 21, 2016).
Raterman et al., The interferon type 1 signature towards prediction of non-response to rituximab in rheumatoid arthritis patients, Arthrit. Res. Ther. 14:r95, 2012.
Rosengren et al., Elevated autoantibody content in rheumatoid arthritis synovia with lymphoid aggregates and the effect of rituximab, Arthrit. Res. Ther. 10:R105, 2008.

(Continued)

*Primary Examiner* — Zachary S Skelding
(74) *Attorney, Agent, or Firm* — Grimes & Yvon LLP

(57) ABSTRACT

The present invention provides a method for determining whether a Rheumatoid Arthritis (RA) patient is susceptible to treatment with a B cell targeted therapy, which method comprises the step of analysing B cells and/or germinal centre-like structures (GC-LS) in a synovial tissue sample from the patient; wherein a patient whose synovial tissue sample is B cell rich and/or GC-LS negative is determined to be susceptible to treatment with the B cell targeted therapy, whereas a patient whose synovial tissue sample is B-cell poor and/or GC-LS positive is determined to be resistant to treatment with the B cell targeted therapy.

6 Claims, 3 Drawing Sheets

(56) References Cited

OTHER PUBLICATIONS

Sellam et al., B Cell Activation Biomarkers as Predictive Factors for the Response to Rituximab in Rheumatoid Arthritis, Arthritis & Rheumatism, 63:933-938, 2011.

Teng et al., Immunohistochemical Analysis as a Means to Predict Responsiveness to Rituximab Treatment, Arthritis & Rheumatism, 56:3909-3918, 2007.

Thurlings et al., Synovial Lymphoid Neogenesis does not define a specific clinical rheumatoid arthritis phenotype, Arthritis & Rheumatism, 58:1582-1589, 2008.

Thurlings et al., Synovial tissue response to rituximab: mechanisn of action and identification of biomarkers or response, Ann. Rheum. Dis. 67:917-925, 2008.

Van Baarsen et al., Synovial Tissue Heterogeneity in Rheumatoid Arthritis in Relation to Disease Activity and Biomarkers . . . , Arthritis & Rheumatism 62:1602-1607, 2010.

Van De Sande et al., Presence of lymphocyte aggregates in the synovium of patients with early arthritis in relationship to diagnosis . . . , Ann. Rheum. Dis. 70:700-703, 2011.

Vital et al., B-Cell and synovial membrane predictors of response and relapse in rheumatoid arthritis patients . . . , Ann. Rheum. Dis., 68 Suppl. 1:A13, Abstract A33, 2009.

Vital et al., Synovial B cell status determines intensity of rituximab therapy required in rheumatoid arthritis, Ann. Rheum. Dis., 72 Suppl 3:OP0045, 2013.

Vos et al., Early Effects of Rituximab on the Synovial Cell Infiltrate in Patients with Rheumatoid Arthritis, Arthritis & Rheumatism, 56:772-778, 2007.

Yannaki et al., The Proteasome Inhibitor Bortezomib Drastically Affects Inflammation and Bone Disease . . . , Arthritis & Rheumatism, 62:3277-3288, 2010.

METHOD FOR TREATING RHEUMATOID ARTHRITIS

FIELD OF THE INVENTION

The invention relates to a method for determining whether a rheumatoid arthritis (RA) patient is susceptible to treatment with a B cell targeted therapy, such as Rituximab. The invention also relates to a method for treating a RA patient who is refractory to B cell targeted therapy.

BACKGROUND TO THE INVENTION

Inflammatory arthritis is a prominent clinical manifestation in diverse autoimmune disorders including rheumatoid arthritis (RA), psoriatic arthritis (PsA), systemic lupus erythematosus (SLE), Sjogren's syndrome and polymyositis.

RA is a chronic inflammatory disease that affects approximately 0.5 to 1% of the adult population in northern Europe and North America. It is a systemic inflammatory disease characterized by chronic inflammation in the synovial membrane of affected joints, which ultimately leads to loss of daily function due to chronic pain and fatigue. The majority of patients also experience progressive deterioration of cartilage and bone in the affected joints, which may eventually lead to permanent disability. The long-term prognosis of RA is poor, with approximately 50% of patients experiencing significant functional disability within 10 years from the time of diagnosis. Life expectancy is reduced by an average of 3-10 years.

Inflammatory bone diseases, such as RA, are accompanied by bone loss around, affected joints due to increased osteoclastic resorption. This process is mediated largely by increased local production of pro-inflammatory cytokines, of which tumor necrosis factor-α (TNF-α) is a major effector.

In RA specifically, an immune response is thought to be initiated/perpetuated by one or several antigens presenting in the synovial compartment, producing an influx of acute inflammatory cells and lymphocytes into the joint. Successive waves of inflammation lead to the formation of an invasive and erosive tissue called pannus. This contains proliferating fibroblast-like synoviocytes and macrophages that produce proinflammatory cytokines such as TNF-α and interleukin-1 (IL-I). Local release of proteolytic enzymes, various inflammatory mediators, and osteoclast activation contributes to much of the tissue damage.

There is loss of articular cartilage and the formation of bony erosions. Surrounding tendons and bursa may become affected by the inflammatory process. Ultimately, the integrity of the joint structure is compromised, producing disability.

B cells are thought to contribute to the immunopathogenesis of RA, predominantly by serving as the precursors of autoantibody-producing cells but also as antigen presenting cells (APC) and pro-inflammatory cytokine producing cells. A number of autoantibody specificities have been identified including antibodies to Type II collagen and proteoglycans, as well as rheumatoid factors and most importantly anti citrullinated protein antibodies (ACPA). The generation of large quantities of antibody leads to immune complex formation and the activation of the complement cascade. This in turn amplifies the immune response and may culminate in local cell lysis.

Current standard therapies for RA which are used to modify the disease process and to delay joint destruction are known as disease modifying anti-rheumatic drugs (DMARDs). Methotrexate, leflunomide and sulfasalazine are traditional DMARDs and are often effective as first-line treatment.

Biologic agents designed to target specific components of the immune system that play role in RA are also used as therapeutics. There are various groups of biologic treatments for RA including; TNF-α inhibitors (etanercept, infliximab and adalimumab), human IL-1 receptor antagonist (anakinra) and selective co-stimulation modulators (abatacept).

Rituximab is indicated for the treatment of moderate to severe RA in adult patients who have had an inadequate response to, or cannot tolerate, one or more TNF-α inhibitor therapies. It has been shown to be effective in the treatment of RA in patients refractory to treatment with anti-TNF therapy.

The Rituximab antibody is a genetically engineered chimeric murine/human monoclonal antibody directed against the CD20 antigen. Rituximab binds human complement and lyses lymphoid B-cell lines through complement-dependent cytotoxicity. Additionally, it has significant activity in assays for antibody-dependent cellular cyotoxicity. More recently, Rituximab has been shown to have anti-proliferative effects in tritiated thymidine-incorporation assays and to induce apoptosis directly. Other anti-CD19 and anti-CD20 antibodies have not been shown to have this activity.

Rituximab treatment has been shown to result in B cell depletion in peripheral blood, bone marrow and the synovium. However, not all patients refractory to treatment with anti-TNF therapy are responsive to Rituximab treatment. Current evidence on the efficacy of Rituximab relates primarily to rheumatoid factor, ACPA positive patients, although even within this population clinical responses are heterogeneous with only 60% achieving an ACR20 response within 6 months.

Rituximab is associated with various safety issues, especially infusion-related adverse events and is also very expensive, costing approximately $10,000 per treatment course.

There is thus a need for a method to predict whether a given RA patient is likely to respond to Rituximab treatment. There is also a need for alternative method of treatment for RA patients who are refractory to treatment with Rituximab.

SUMMARY OF ASPECTS OF THE INVENTION

Figure 1:
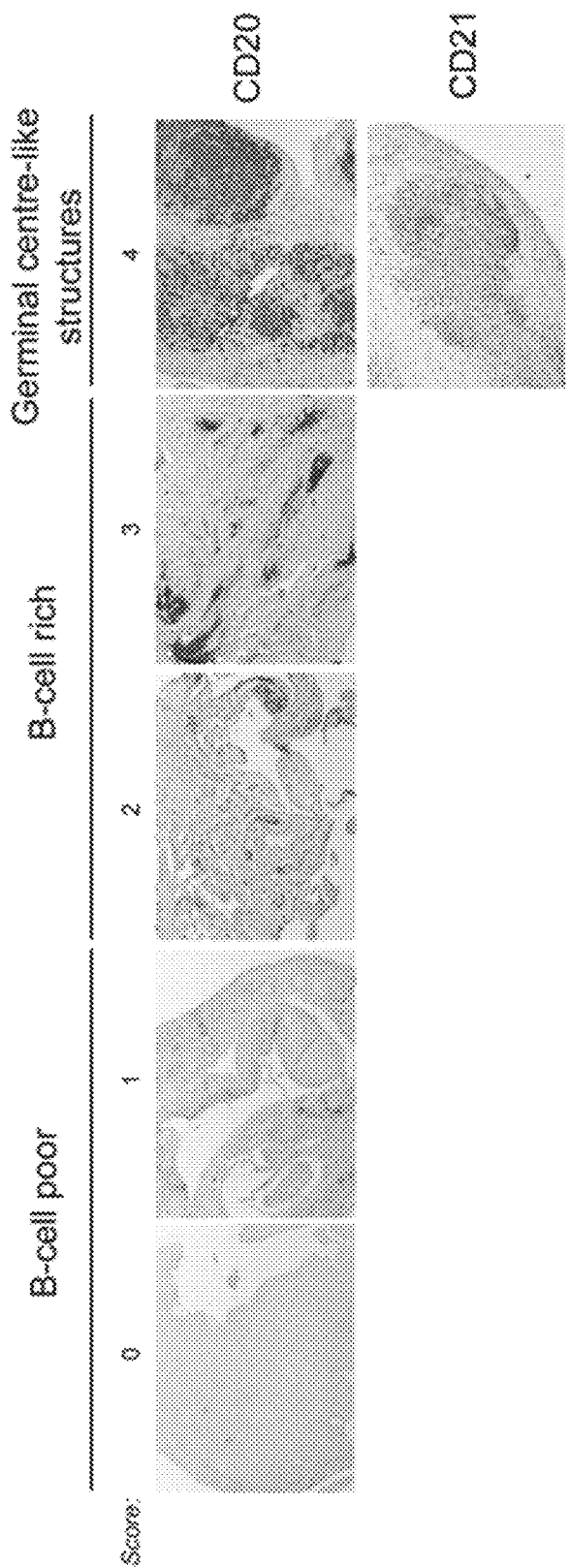
FIG. 1—immunohistochemical staining of tissue biopsy samples used in an exemplar B cell scoring system. Staining for CD20 was used to quantitatively assess the presence of B cells in RA synovial samples, being classified as B cell poor (score from 0 to 1) and B cell rich (score from 2-3) as is shown in the example images. CD21 expression was assessed in samples displaying a CD20 score of 4 and were positive for. GC-LS/FDC networks when a cluster of CD21+ cells was detected. Original magnification ×10.

The present inventors have made the surprising finding that the histomorphological type of a synovial sample from a RA patient is predictive of the patient's response to B cell targeted therapy.

Due to the systemic nature of RA, it was thought an assessment of biomarkers in peripheral blood was important for identification and stratification of patients who would respond to B cell targeted therapy (Owczarczyk et al. *Sci. Transl. Med.* 2011; 3:101ra92, Sellam et al. *Arthritis & Rheumatism* 2011; 63(4):933-938). The present invention, however, now shows that rather than looking at markers in blood, B cell levels and morphology in the synovium are predictive of a RA patient's response to B cell targeted therapy.

In a first aspect, the present invention relates to a method for determining whether a Rheumatoid Arthritis (RA) patient is susceptible to treatment with a B cell targeted therapy, which method comprises the step of analysing B cells and/or germinal centre-like structures (GC-LS) in a synovial tissue sample from the patient; wherein a patient whose synovial tissue sample is B cell rich and/or GC-LS negative is determined to be susceptible to treatment with the B cell targeted therapy, whereas a patient whose synovial tissue sample is B-cell poor and/or GC-LS positive is determined to be resistant to treatment with the B cell targeted therapy.

The step of analysing B cells and/or GC-LS may be performed by histological analysis. A patient whose synovial tissue sample is B cell poor may be characterised by a diffuse pattern of a small number of B cells interspersed with prevalent myeloid inflammatory infiltrate, while a patient whose synovial tissue sample is B cell rich may be characterised by the clustering of B cells in an aggregated pattern. A patient who is GC-LS positive may be characterised by the presence of B cell aggregates and detection of CD21 within said aggregates.

B cells may be analysed by determining CD20 expression or other markers in the synovial sample.

The B cell targeted therapy may be B cell depletion therapy. The B cell targeted therapy may be selected from the following list: Rituximab, Ocrelizumab, Veltuzumab, Ofatumumab and Epratuzumab.

The B cell targeted therapy may be Rituximab.

A patient whose synovial tissue sample is GC-LS positive may be resistant to Rituximab therapy and determined to be suitable for treatment with an agent which downregulates IL-6 mediated signaling. The agent that downregulates IL-6 signaling may be an IL-6 receptor antagonist, for example the agent may be Tocilizumab.

The method of the present invention may be performed using a synovial sample from a RA patient who is refractory to synthetic or biologic (e.g. anti-TNF) DMARD therapies.

In a second aspect the present invention provides a kit for use in a method according to the first aspect.

In a third aspect the present invention provides a method for treating a Rheumatoid Arthritis (RA) patient who is refractory to treatment with a B cell targeted therapy which comprises the step of disrupting germinal centre-like structures (GC-LS) in the synovium.

The GC-LS may be disrupted by treatment with an agent which downregulates IL-6 mediated signaling, a proteasome inhibitor or a growth factor inhibitor.

DETAILED DESCRIPTION

Rheumatiod Arthritis

RA is a chronic, systemic inflammatory disorder that may affect many tissues and organs, but principally attacks synovial joints. It is a disabling and painful condition, which can lead to substantial loss of functioning and mobility if not adequately treated.

The disease process involves an inflammatory response of the synovium, secondary to massive immune cell infiltration and proliferation of synovial cells, excess synovial fluid, and the development of fibrous tissue (pannus) in the synovium that attacks the cartilage and, sub-chondral bone. This often leads to the destruction of articular cartilage and the formation of bone erosions with secondary ankylosis (fusion) of the joints. RA can also produce diffuse inflammation in the lungs, the pericardium, the pleura, the sclera, and also nodular lesions, most commonly in subcutaneous tissue. RA is considered a systemic autoimmune disease as autoimmunity plays a pivotal role in its chronicity and progression.

The term synovial sample refers to a sample derived from a synovial joint. Typically the synovial sample will be derived for a synovial joint of a RA patient. A synovial sample may be a synovial tissue biopsy and the synovial joint may display active inflammation at the time the sample is taken.

A number of cell types are involved in the aetiology of RA, including T cells, B cells, monocytes, macrophages, dendritic cells and synovial fibroblasts. Autoantibodies known to be associated with RA include those targeting Rheumatoid factor (RF) and anti citrullinated protein antibodies (ACPA).

RA Therapy

A typical patient with newly diagnosed RA is often treated initially with nonsteroidal anti-inflammatory drugs and disease-modifying antirheumatic drugs (DMARDs) such as hydroychloroquine, sulfasalazine, letlunomide, or methotrexate (MTX), alone or in combinations. Patients who do not respond to general DMARDs may be termed DMARD-refractory.

DMARD-refractory patients are often progressed to biological therapeutic agents, for example TNF-α antagonists such as Adalimumab, Etanercept, Golimumab and Infliximab. Patients who do not respond to TNF-α antagonist therapy may be termed TNF-α antagonist-refractory or inadequate responders (ir).

The method of the present invention may be performed on a synovial sample from a RA patient who has previously been determined to be refractory to DMARD-therapy and/or TNF-α antagonist therapy. The method may also be performed on a synovial sample from a RA patient unable to tolerate TNF-α antagonist therapy.

B Cells

B cells play a central role in the pathogenesis of RA.

Immature B cells' are produced in the bone marrow. After reaching the IgM$^+$ immature stage in the bone marrow, these immature B cells migrate to secondary lymphoid tissues (such as the spleen, lymph nodes) where they are called transitional B cells, and some of these cells differentiate into mature B lymphocytes and possibly plasma cells.

B cells may be defined by a range of cell surface markers which are expressed at different stages of B cell development and maturation (Table 1). These B cell markers may include CD19, CD20, CD22, CD23, CD24, CD27, CD38, CD40, CD72, CD79a and CD79b, CD138 and immunoglobulin (Ig).

TABLE 1

| Compartment | Cell Type | Markers |
|---|---|---|
| Bone marrow | Stem cell | |
| | Pro-B cell | CD19$^+$ CD20$^-$ Ig$^-$ |
| | Pre-B cell | CD19$^+$ CD20$^+$ Ig$^-$ |
| | Immature B cell | CD19$^+$ CD20$^+$ Ig$^+$ |

TABLE 1-continued

| Compartment | Cell Type | Markers |
|---|---|---|
| Peripheral compartments | Naïve B cell | $CD19^+$ $CD20^+$ $Ig^+$ $CD38^{+/-}$ |
| | Naïve activated B cell | $CD19^+$ $CD20^+$ $Ig^+$ $CD38^+$ |
| | GC B cell | $CD19^+$ $CD20^+$ $Ig^+$ $CD38^{++}$ |
| | Post-GC B cell | $CD19^+$ $CD20^+$ $Ig^+$ $CD38^+$ |
| | Memory B cell | $CD19^+$ $CD20^+$ $Ig^{+/-}$ $CD27^+$ $IgM/IgG/IgA^+$ $CD38^-$ |
| | Plasma blast | $CD19^+$ $CD20^-$ $Ig^{+/-}$ $CD27^{++}$ $CD38^{++}$ |
| Bone marrow | Plasma cell | $CD19^{+/-}$ $CD20^-$ $Ig^-$ $CD27^{++}$ $CD38^{+++}$ $CD138^+$ |

Immunoglobulins (Ig) are glycoproteins belonging to the immunoglobulin superfamily which recognise foreign antigens and facilitate the humoral response of the immune system. Ig may occur in two physical forms, a soluble form that is secreted from the cell, and a membrane-bound form that is attached to the surface of a B cell and is referred to as the B cell receptor (BCR). Mammalian Ig may be grouped into live classes (isotypes) based on which heavy chain they possess. Immature B cells, which have never been exposed to an antigen, are known as nave B cells and express only the IgM isotype in a cell surface bound form. B cells begin to express both IgM and IgD when they reach maturity—the co-expression of both these immunoglobulin isotypes renders the B cell 'mature' and ready to respond to antigen. B cell activation follows engagement of the cell bound antibody molecule with an antigen, causing the cell to divide and differentiate into an antibody producing plasma cell. In this activated form, the B cell starts to produce antibody in a secreted form rather than a membrane-bound form. Some daughter cells of the activated B cells undergo isotype switching to change from IgM or IgD to the other antibody isotypes, IgE, IgA or IgG, that have defined roles in the immune system.

CD19 is expressed by essentially all B-lineage cells and regulates intracellular signal transduction by amplifying Src-family kinase activity.

CD20 is a mature B cell-specific molecule that functions as a membrane embedded $Ca^{2+}$ channel. Expression of CD20 is restricted to the B cell lineage from the pre-B-cell stage until terminal differentiation into plasma cells.

CD22 functions as a mammalian lectin for α2,6-linked sialic acid that regulates follicular B-cell survival and negatively regulates signaling.

CD23 is a low-affinity receptor for IgE expressed on activated B cells that influences IgE production.

CD24 is a GPI-anchored glycoprotein which was among the first pan-B-cell molecules to be identified.

CD27 is a member of the TNF-receptor superfamily. It binds to its ligand CD70, and plays a key role in regulating B-cell activation and immunoglobulin synthesis. This receptor transduces signals that lead to the activation of NP-κB and MAPK8/JNK.

CD38 is also known as cyclic ADP ribose hydrolase. It is a glycoprotein that also functions in cell adhesion, signal transduction and calcium signaling and is generally a marker of cell activation.

CD40 serves as a critical survival factor for germinal centre (GC) B cells and is the ligand for CD154 expressed by T cells.

CD72 functions as a negative regulator of signal transduction and as the B-cell ligand for Semaphorin 4D (CD100).

CD79a/CD79b dimer is closely associated with the B-cell antigen receptor, and enables the cell to respond to the presence of antigens on its surface. The CD79a/CD79b dimer is present on the surface of B-cells throughout their life cycle, and is absent on all other healthy cells.

CD138 is also known as Syndecan 1. Syndecans mediate cell binding, cell signaling, and cytoskeletal organization. CD138 may be useful as a cell surface marker for plasma cells.

The method of the present invention comprises the step of analysing the presence of B cells in a synovial sample from a RA patient and determining if a RA patient is B cell rich or B cell poor. This analysis may involve determining the presence of cells expressing one or more of the markers detailed in Table 1.

The presence of B cells may be determined by analysing the level and pattern of B cells in a synovial sample from a RA patient. Such analysis may be performed by histological analysis.

The identification of RA patients who are B cell rich or B cell poor may be performed by using a system for grading lymphocytic aggregates known to those skilled in the art. In the examples section, the present inventors use a system adapted from the one described in their previous publication (Manzo et al. *Eur. J. Immunol.* (2005); 35(5):1347-1359). The radial cell count is estimated by counting the number of cells from the more centrally located vessel to the identifiable edge of its aggregate. The determination is made at the point of widest infiltration.

The maximum lymphocytic aggregate identified may be graded according to the maximum radial cell count measured from the central vessel as described by Manzo et al. (as above). Aggregates may be categorised into three groups according to the radial cell count as shown in Table 5 and the grading atlas provided as FIGS. 2 and 3.

TABLE 5

| Grade | Radial Cell Count |
|---|---|
| 0 Uninflamed/Diffuse | No aggregates visualised |
| 1 | 2-5 cells |
| 2 | 6-10 cells |
| 3 | >10 cells |

Figure 2:
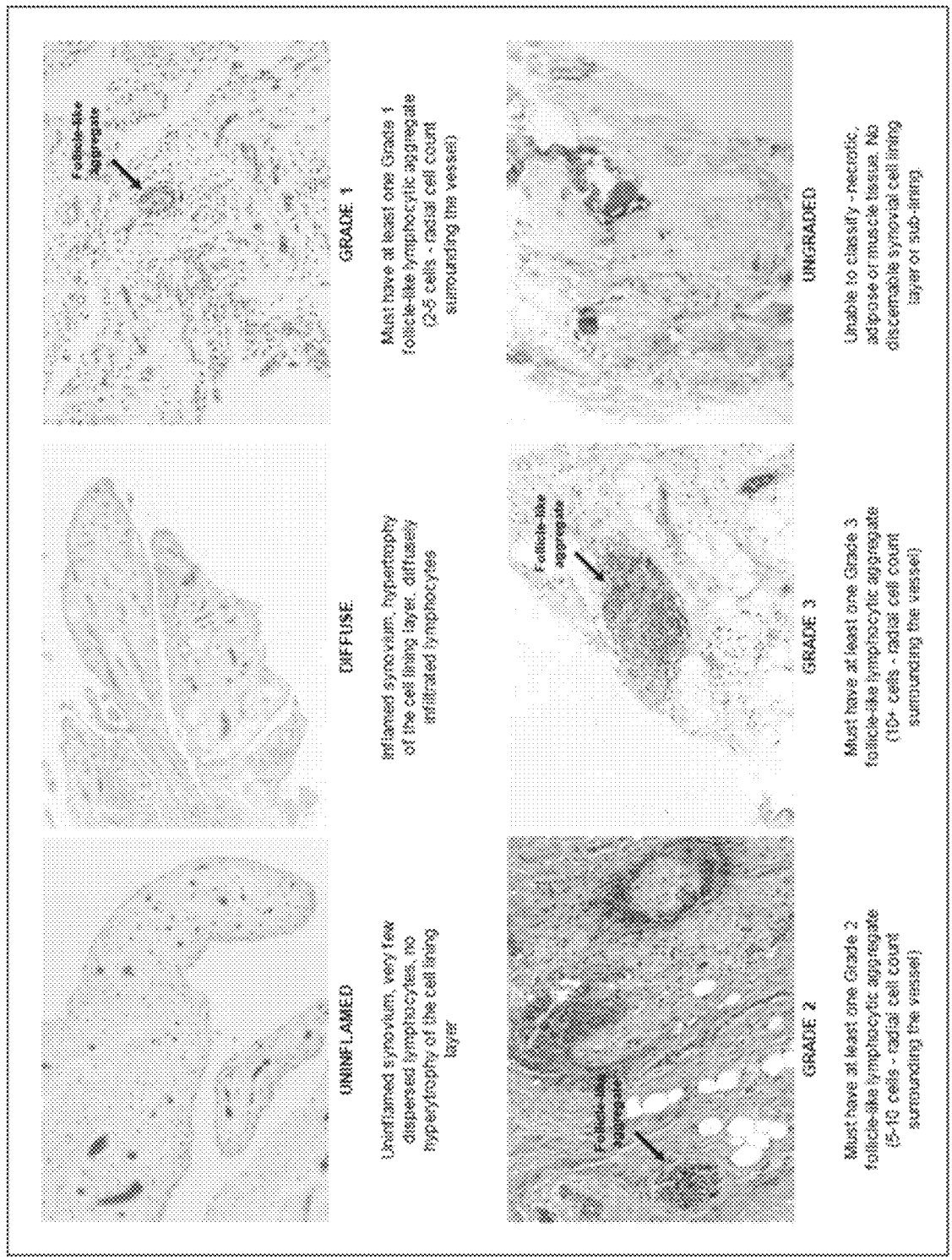
FIG. 2—Atlas 1: Scoring of aggregates on H&E specimens using a 0-3 scale

Depending on the numbers of B cell identified per high power field (HPF), biopsies are thus classified as B cell poor (Grade 0 and 1), B cell rich (Grade 2 and 3) and Germinal Center (GC) rich Grade 4+CD 21 positivity (see Atlas 1, FIG. 2).

Figure 3:
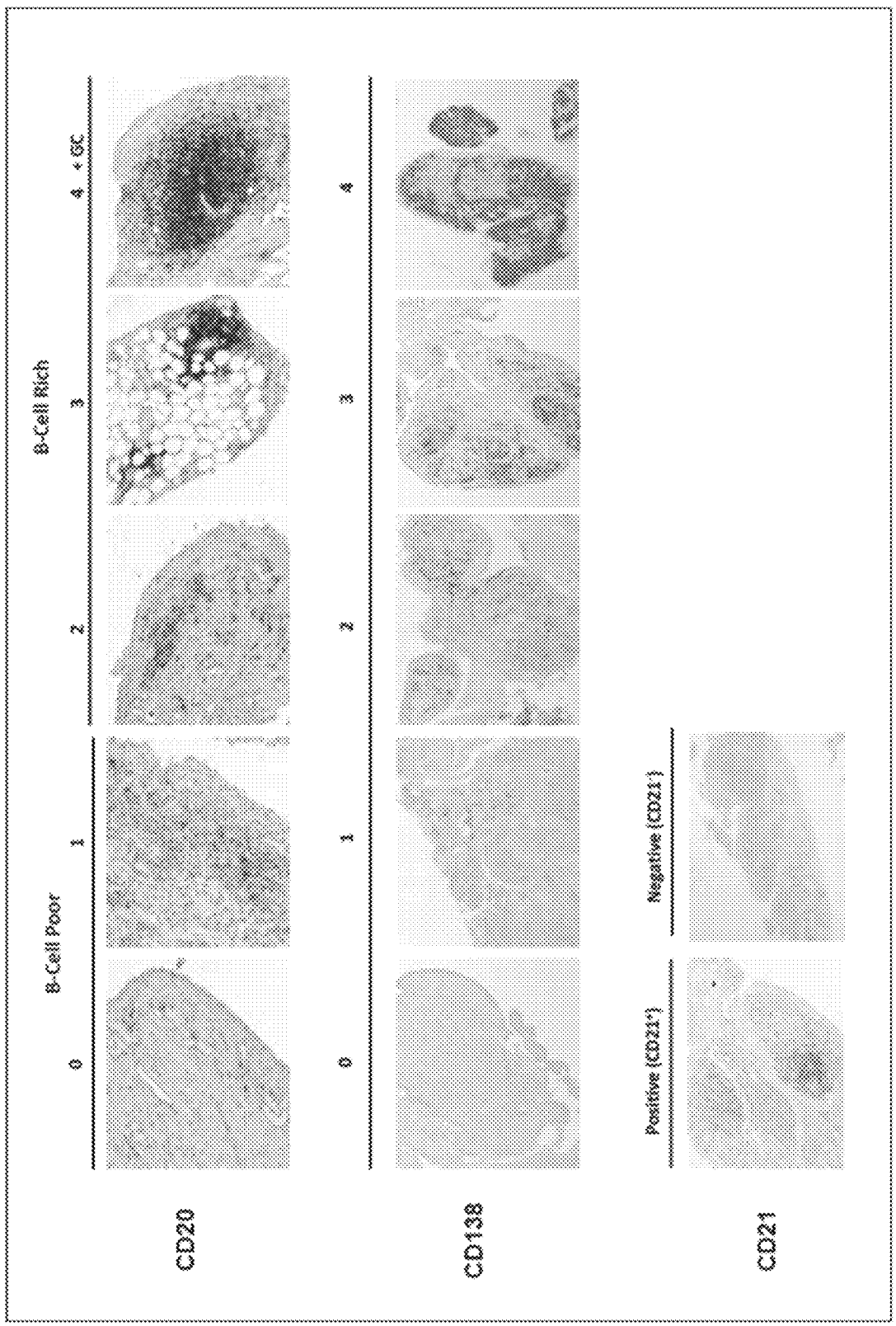
FIG. 3—Atlas 2: Scoring of CD20, CD138 and CD21 by immunohistochemistry scoring analysis

Such a grading system may also be used in combination with analysis of B cell surface markers, for example CD20 and/or CD79a (see Atlas 2, FIG. 3).

The presence of B cells within a synovial sample from a RA patient may be determined by analysing the level of B cell markers within the sample using techniques such as next-generation sequencing, gene expression arrays, PCR and proteomics. Such techniques may be used assess the level of a B cell marker RNA and/or protein within the synovial sample, with an increased level of the B cell marker determining a B cellrich profile. The B cell marker may be, for example, CD20 and/or CD79a. The synovial sample may be a synovial tissue biopsy.

Germinal Centre-Like Structures (GC-LS)

The method of the present invention may comprise the step of analysing the presence of GC-LS in a synovial sample from a RA patient.

Germinal centres are sites where mature B cells rapidly proliferate, differentiate, and undergo somatic hyperinutation and class switch recombination during an immune response. During this process of rapid division and selection, B cells are known as centroblasts, and once they have stopped proliferating they are known as centrocytes. B cells within germinal centres express CD138 when they differentiate into plasma cells. Germinal centres develop dynamically after the activation of B cells by T-cell dependent antigen.

The term GC-LS refers to an ectopic or tertiary lymphatic structure that forms in non-lymphoid tissues and may develop to become a place of autoantibody generation. In the context of RA, the GC-LS form in the synovium. GC-LS are typically characterised by the presence of aggregated T and/or B lymphocytes alongside follicular dendritic cells (FDCs).

FDCs have high expression of complement receptors CR1 and CR2 (CD35 and CD21 respectively) and Fc-receptor FcγRIIb (CD32). Further FDC specific molecular markers include FDC-M1, FDC-M2 and C4.

The identification of GC-LS in a synovial sample of a RA patient may therefore involve determining the presence of cells positive for one or more of the above markers. For example it may involve determining the presence of plasma cells ($CD138^+$) and/or FDCs ($CD35^+$-$CD21^+$).

The identification of GC-LS may be performed using the immunohistochemistry scoring analysis as provided in Atlas 2 (FIG. 3).

Determining the presence of GC-LS in a synovial sample of a RA patient may involve identifying FDCs within B cell aggregates using one or more of the above markers. Determining the presence of GC-LS may involve the identification of $CD21^+$ cells within B cell aggregates in a synovial sample from a RA patient.

B Cell Targeted Therapy A RA patient identified as B cellrich and/or GC-LS negative by the method of the present invention is determined as being susceptible to treatment with a B cell targeted therapy whereas a patient who is B-cell poor and/or GC-LS positive is determined as resistant to treatment with a B cell targeted therapy.

A B cell targeted therapy refers to the administration of an agent that interferes with or inhibits the development and/or function of B cells. The B cell targeted therapy may cause B cell depletion or the inhibition of B cell development and maturation. Advantageously, the B cell targeted therapy is directed against B cells in all stages of development other than undifferentiated stem cells and terminally differentiated antibody-producing plasma cells.

The agent may be a small molecule drug, such as a Bruton's tyrosine kinase (BTK) inhibitor or other agent which targets B cell signaling pathways.

Direct depletion of B cells may be performed through the use of monoclonal antibodies (mAbs) directed against cell surface markers (e.g. CD20 and CD22). Such mAbs bind to the target antigen and kill the cell by initiating a mixture of apoptosis, complement dependent cytotoxicity (CDC), and antibody-dependent cell-mediated cellular cytotoxicity (ADCC).

The B cell targeted therapy used in the present invention may be an agent directed against CD20, for example Rituximab, Ocrelizumab, Veltuzumab or Ofatumumab, or an agent directed against CD22 such as Epratuzumab.

Rituximab is a chimeric mouse/human immunoglobulin G1 (IgG1) monoclonal antibody to CD20 that stimulates B cell destruction upon binding to CD20. Rituximab depletes CD20 surface-positive nave and memory B cells from the blood, bone marrow and lymph nodes via mechanisms which include antibody-dependent cellular cytotoxicity (ADCC), complement dependent cytotoxicity (CDC). It does not affect CD20-negative early B cell lineage precursor cells and late B lineage plasma cells in the bone marrow.

Ocrelizumab is a humanized anti-CD20 monoclonal antibody that causes $CD20^+$ B cell depletion following binding to CD20 via mechanisms including ADCC and CDC.

Veltuzumab is a humanized, second-generation anti-CD20 monoclonal antibody that causes $CD20^+$ B cell depletion following binding to CD20 via mechanisms including ADCC and CDC.

Ofatumumab is a human monoclonal IgG1 antibody to CD20 and may inhibit early-stage B lymphocyte activation. Ofatumumab targets a different epitope located closer to the N-terminus of CD20 compared to the epitope targeted by rituximab and includes an extracellular loop, as it binds to both the small and large loops of the CD20 molecule. Ofatumumab stimulates B cell destruction through ADCC and CDC pathways.

Epratuzumab is a humanized monoclonal IgG1 antibody to CD22. It contains a murine sequence comprising 5-10% of the molecule, the remainder being human framework sequences. Epratuzumab binds to the CD22 third extracellular domain (epitope B), without blocking the ligand binding site, with measured affinity of $K_d$=0.7 nm. In vitro studies showed epratuzumab induces CD22 phosphorylation by binding to its surface. It results in modulation, mostly negative, of BCR activation.

IL-6 Mediated Signaling

In a further aspect, a RA patient identified by the method of the present invention as GC-LS positive is determined to be suitable for treatment with an agent which downregulates interleukin-6 (IL-6) signaling.

IL-6 is a cytokine that provokes a broad range of cellular and physiological responses, including inflammation, hematopoiesis, and oncogenesis by regulating cell growth, gene activation, proliferation, survival, and differentiation. It is able to directly influence B cell activation state and late stage differentiation towards plasma cells.

IL-6 signals through a receptor composed of two different subunits, an alpha subunit that produces ligand specificity and GP (Glycoprotein) 130, a receptor subunit shared in common with other cytokines in the IL-6 family. Binding of IL-6 to its receptor initiates cellular events including activation of JAK (Janus Kinase) kinases and activation of Ras-mediated signaling. Activated JAK kinases phosphorylate and activate STAT transcription factors, particularly STAT3 and SHP2. Phosphorylated STAT3 then forms a dimer and translocates into the nucleus to activate transcription of genes containing STAT3 response elements. STAT3 is essential for GP130-mediated cell survival and G1 to S cell-cycle-transition signals. Both e-Myc and Pim have been identified as target genes of STAT3 and together can compensate for STAT3 in cell survival and cell-cycle transition. SHP2 links cytokine receptor to the Ras/MAP (Mitogen-Activated Protein) kinase pathway and is essential for mitogenic activity.

The Ras-mediated pathway, acting through SHC, GRB2 (Growth Factor Receptor Bound protein-2) and SOS1 (Son of Sevenless-1) upstream and activating MAP kinases downstream, activates transcription factors such as Elk1 and NF-IL-6 (C/EBP-β) that can act through their own cognate response elements in the genome.

In addition to JAK/STAT and Ras/MAP kinase pathways, IL-6 also activates PI3K (Phosphoinositide-3 Kinase). The PI3KJAkt/NF-KappaB cascade activated by IL-6, functions cooperatively to achieve the maximal anti-apoptotic effect of IL-6 against TGF-β. The anti-apoptotic mechanism of PI3K/Akt is attributed to phosphorylation of the BCL2 family member BAD (BCL2 Associated Death Promoter) by Akt. The phosphorylated BAD is then associated with 14-3-3, which sequesters BAD from BCLXL, thereby promoting cell survival. Regulating the BCL2 family member is also considered as one of the anti-apoptotic mechanisms of STAT3, which was may be capable of inducing BCL2 in pro-B cells. The termination of the IL-6-type cytokine signaling is through the action of tyrosine phosphatases, proteasome, and JAK kinase inhibitors SOCS (Suppressor of Cytokine Signaling), PIAS (Protein Inhibitors of Activated STATs), and internalization of the cytokine receptors via GP130.

An agent which downregulates IL-6 signaling may interfere with or inhibit any of the above stages involved in IL-6 mediated signaling such that IL-6 signaling and responses are diminished. For example the agent may be an IL-6 receptor antagonist such as Tocilizumab, which is a humanized monoclonal antibody against the IL-6 receptor. An IL-6 receptor antagonist refers to an agent that reduces the level of IL-6 that is able to bind to the IL-6 receptor.

The present invention also provides a method for treating a RA patient who is refractory to treatment with a B cell targeted therapy, which comprises the step of disrupting GC-LS in the synovium.

The GC-LS may be disrupted by treatment with an agent which downregulates IL-6 mediated signaling, for example Tocilizumab.

Tocilizumab is a humanized monoclonal IgG1 antibody against the IL-6 receptor that binds to soluble and membrane-bound IL-6 receptor. Tocilizumab inhibits the induction of biological activity due to IL-6 in cells that have expressed both membrane-bound IL-6 receptor and gp130 molecules, and also inhibits the induction of biological activity due to IL-6/IL-6 receptor complex formation in cells that express gp130 alone. Furthermore, since it has the capacity to dissociate IL-6/IL-6 receptor complexes that have already formed, it is able to block IL-6 signal transduction.

The GC-LS may be disrupted by treatment with a growth factor inhibitor or an agent that inhibits signaling required for B cell function. The agent may, for example, inhibit B-cell activating factor (BAFF) or a proliferation-inducing ligand (APRIL) signaling. Examples of such agents include, but are not limited to, Belimumab and Atacicept.

Belimumab is a human monoclonal IgG1λ antibody that inhibits BAFF (also known as, B-lymphocyte stimulator (BLyS)). BAFF is a 285-amino acid type II protein that is a member of the TNF ligand superfamily and is a vital B cell survival factor, with important roles in the differentiation of immature to mature B cells and in immunoglobulin class switching and production. Belimumab inhibits B cell survival and differentiation by neutralizing soluble BAFF, without directly causing B celldeath.

Atacicept is a fully human recombinant fusion protein containing the extracellular ligand-binding portion of the TACI (Transmembrane Activator and CAML [calcium-modulator and cyclophilin-ligand]-Interactor) receptor and a modified Fc portion of human IgG. Atacicept, therefore, contains the binding portion of a receptor that binds both BAFF and APRIL. APRIL is a structural homologue of BAFF that is secreted as a soluble protein by monocytes, macrophages, dendritic cells, neutrophils and T cells, and shares some of the biological properties of BAFF.

The GC-LS may be disrupted by a proteasome inhibitor such as Bortezomib.

Bortezomib is an N-protected dipeptide that binds the catalytic site of the 26S proteasome, thereby inhibiting proteasome function. The proteasome regulates protein expression and function by degradation of ubiquitylated proteins, and also removes abnormal or misfolded proteins from the cell.

Kit

The present invention also provides a kit for use in a method of determining whether a RA patient is susceptible to treatment with a B cell targeted therapy, which method comprises the step of analysing the presence of B cells and/or germinal centre-like structures (GC-LS) in a synovial tissue sample from the patient;

wherein a patient whose synovial tissue sample is B cell rich and/or GC-LS negative is determined to be susceptible to treatment with the B cell targeted therapy, whereas a patient whose synovial tissue sample is B-cell poor and/or GC-LS positive is determined to be resistant to treatment with the B cell targeted therapy.

The kit may comprise;
i) An agent for the detection of B cells in a synovial sample of a RA patient,
ii) An agent for the detection of GC-LS in a synovial sample of a RA patient.

Agents for the detection of B cells in a synovial sample from a RA patient may include agents that detect CD20 and/or CD79a.

Agents for the detection of GC-LS in a synovial sample of a RA patient may include agents that detect CD21.

The kit may also comprise instructions for use.

The kit may also comprise a B cell targeted therapy or an agent that downregulates IL-6 signaling.

The invention will now be further described by way of Examples, which are meant to serve to assist one of ordinary skill in the art in carrying out the invention and are not intended in any way to limit the scope of the invention.

EXAMPLES

Example 1

An Investigation Into the Molecular Mechanisms Predicting Response to Rituximab in RA Patients Resistant to Anti-TNF Therapy Aims This was an open-label, ultrasound guided synovial biopsy-based study of RA patients. The primary aim was to investigate in anti-TNFα inadequate responders whether baseline synovial pathobiological phenotypes defined specific response/resistance subsets to Rituximab therapy.

Results

Patient demographics of 27 patients recruited are shown in Table 2.

TABLE 2

Patient demographics of total study population (n = 27)

| | No (%) |
| --- | --- |
| Female | 21 (77) |
| Rheumatoid factor +ve | 24 (88) |

TABLE 2-continued

| Patient demographics of total study population (n = 27) | |
| --- | --- |
| CCP +ve | 25 (97) |
| Erosive | 25 (97) |
| | Mean +/− St Dev |
| Age | 59.1 (+/− 14.1) |
| Baseline DAS | 6.1 (+/−1.6) |

A preliminary analysis of the first 21 patients recruited to the study classified patients into either an aggregate or diffuse synovial histological pattern and numbers of responders/non-responders within each histological group were determined (Table 2). Results were analysed using Fisher's exact test and demonstrated a significant difference in response between groups (p=0.014), with a significantly higher percentage of aggregate (83%) versus diffuse (20%) patients responding to Rituximab treatment.

TABLE 3

Response to Rituximab is significantly associated with an aggregate histological pattern and non-response is significantly associated with a diffuse infiltrate in TNF inadequate responders (n = 21, p = 0.014).

| Clinical response to Rituximab | Synovial Histomorphological Pattern | |
| --- | --- | --- |
| | Aggregate number (%) | Diffuse number (%) |
| Responder | 5 (83) | 3 (20) |
| Non-responder | 1 (17) | 12 (80) |

All 27 patients were classified as B cell rich, B cell poor or germinal centre like structures (GC-LS) positive (+ve). Numbers of responders and non-responders within each histological group were identified and results analysed using Fisher's exact test (Table 4). A significant difference (p=0.032) was seen between the percentage of patients responding to Rituximab in the B cell poor (22%) versus B cell rich (80%) group. In addition within the group of patients classified as GC-LS positive there was a trend towards non-response to Rituximab (75% non-responders vs 25% responders).

TABLE 4

Immunohistological classification of synovial tissue as B cell rich. B cell poor or Germinal centre demonstrates a significant difference in levels of response to Rituximab within B cell rich and B cell poor patients (n = 27, p = 0.032).

| Clinical response to Rituximab | Synovial Histomorphological Pattern | | |
| --- | --- | --- | --- |
| | Germinal Centre +ve n (%) | B cell rich n (%) | B cell poor n (%) |
| Responder | 1 (25) | 4 (80) | 4 (22) |
| Non-responder | 3 (75) | 1 (20) | 14 (78) |

Materials and Methods
Patients and Samples

At baseline patients underwent a minimally invasive ultrasound guided synovial biopsy of an actively inflamed joint. Baseline clinical data was collected including age, sero positivity for rheumatoid factor, anti-CCP antibody status, disease activity score (DAS) of 28 joint count and radiographs of hands and feet. Patients were infused with standard Rituximab therapy (2×1 g Rituximab therapy at a fortnightly interval) within 2 weeks of the biopsy. DAS-28 assessment along with routine bloods following Rituximab therapy were performed on a monthly basis for 12 months. Patients were classified as responders to treatment at 3 months according to EULAR response criteria and responders were eligible for re-treatment at 6 and 12 month time points. Non-responders to Rituximab were switched to other biologic drugs according to NICE guidelines (TA195 and TA198).

The primary outcome measure was the number of responders at 3 months within each histomorphological subgroup.

Histological Grading of Tissues

Synovial tissue specimens were immediately fixed in 4% formalin. Alter paraffin embedding, 3 μm serial sections underwent routine H&E staining in order to define the predominant histological pattern of RA synovitis as either diffuse or aggregate. Lymphocytic aggregates were classified into three groups based on a scoring system the present inventors had adapted from their previous publication (Manzo et al. *Eur. J. Immunol.* (2005); 35(5):1347-1359). Depending on the numbers of B cell identified per high power field (HPF), biopsies were classified as B cell poor (Grade 0 and 1), B cell rich (Grade 2 and 3) and Germinal Center (GC) rich. Grade 4+CD 21 positive.

In addition, formalin-fixed, paraffin-embedded tissue sections underwent immunohistochemical staining. Following antigen retrieval with Target retrieving solution (DAKO) sections were stained for CD20 (IgG2a, clone L26; DAKO) at an antibody dilution of 1:20 and following proteinase K digestion (DAKO) single staining for CD21 (IF8, DAKO) at a dilution of 1:20 was also performed to identify FDC networks (CD21 +ve) characterising germinal centre like structures (GC-LS). Based on the results of the CD21 staining and the presence of G2/G3 aggregates, samples were qualitatively classified as either B cell poor (diffuse), or B cellrich (CD21−ve) or germinal centre positive (CD21 +ve) (FIG. 1). The grading was performed at ×10 magnification over the whole sublining area available for each section and by 2 independent observers with excellent correlation (Intra class correlation coefficient for repeated measurements of B cell score 0.96).

Statistical Analysis

Numbers of patients classified as responders and non-responders within each histological group was determined and significant differences between groups analysed using Fisher's exact test. P values <0.05 were taken as significant. Intra class correlation coefficients were used to determine reliability of B cell score between two observers.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular biology, histology or related fields are intended to be within the scope of the following claims.

The invention claimed is:

1. A method for treating a Rheumatoid Arthritis (RA) patient resistant to treatment with a B cell targeted therapy, which method comprises the steps of: (a) identifying an RA patient resistant to treatment with a B cell targeted therapy by analysing B cells and/or germinal centre-like structures (GC-LS) in a synovial tissue sample from an RA patient, wherein analysing B cells and GC-LS is performed by histological analysis; wherein a patient whose synovial tissue sample is B cell poor and/or GC-LS positive is resistant to treatment with a B cell targeted therapy; wherein the B cell poor synovial tissue sample is characterised by an absence of B cell aggregates with a radial cell count of 6 cells or greater measured from a central vessel at the point of widest infiltration; wherein the GC-LS positive synovial tissue sample is characterised by the presence of B cell aggregates and detection of CD21 within said aggregates; and (b) administering an agent which downregulates IL-6 mediated signalling.

2. The method of claim 1, wherein B cells are analysed by determining CD20 expression in the synovial tissue sample.

3. The method of claim 1, wherein the agent which downregulates IL-6 mediated signalling is an IL-6 receptor antagonist.

4. The method of claim 3, wherein the agent is Tocilizumab.

5. The method of claim 1, wherein GC-LS are disrupted by treatment with an agent which downregulates IL-6 mediated signalling.

6. The method of claim 1, wherein the RA patient is refractory to anti-TNF therapy.

* * * * *